(12) United States Patent
Dozortsev et al.

(10) Patent No.: US 8,268,162 B2
(45) Date of Patent: Sep. 18, 2012

(54) VOLTAMMETRIC DEVICE HAVING SAMPLE DEGASSING SYSTEM

(75) Inventors: Vladimir Dozortsev, Seattle, WA (US); William T. Dietze, Seattle, WA (US)

(73) Assignee: TraceDetect, Inc., Seattle, WA (US)

( * ) Notice: Subject to any disclaimer, the term of this patent is extended or adjusted under 35 U.S.C. 154(b) by 0 days.

(21) Appl. No.: 12/862,549

(22) Filed: Aug. 24, 2010

(65) Prior Publication Data

US 2011/0210752 A1 Sep. 1, 2011

Related U.S. Application Data

(63) Continuation of application No. PCT/US2009/032164, filed on Jan. 27, 2009.

(60) Provisional application No. 61/031,607, filed on Feb. 26, 2008.

(51) Int. Cl.
G01N 27/403 (2006.01)

(52) U.S. Cl. ............ 205/789.5; 205/775; 205/789; 204/400; 204/416

(58) Field of Classification Search .......... 204/400, 204/403.01, 416–419, 434, 409–412; 205/775, 205/789, 789.5
See application file for complete search history.

(56) References Cited

U.S. PATENT DOCUMENTS

| | | | | |
|---|---|---|---|---|
| 3,904,487 A | * | 9/1975 | Lieberman et al. | 205/789.5 |
| 4,058,446 A | * | 11/1977 | Zirino et al. | 204/409 |
| 4,915,713 A | | 4/1990 | Buzza | |
| 5,190,627 A | * | 3/1993 | Saito et al. | 204/158.2 |
| 5,344,500 A | | 9/1994 | Sasaki | |
| 6,664,776 B2 | | 12/2003 | Olofsson | |

OTHER PUBLICATIONS

International Search Report mailed Jun. 30, 2009, issued in corresponding International Application No. PCT/US2009/032164, filed Jan. 27, 2009.

\* cited by examiner

*Primary Examiner* — Alex Noguerola
(74) *Attorney, Agent, or Firm* — Christensen O'Connor Johnson Kindness PLLC

(57) ABSTRACT

A system and method for voltammetric analysis of a liquid sample solution.

37 Claims, 9 Drawing Sheets

VOLTAMMETRIC DEVICE HAVING SAMPLE DEGASSING SYSTEM

CROSS-REFERENCES TO RELATED APPLICATION

This application is a continuation of International Application No. PCT/US2009/032164, filed Jan. 27, 2009, which claims the benefit of U.S. Provisional Application No. 61/031,607, filed Feb. 26, 2008. Each application is incorporated herein by referenced in its entirety.

FIELD OF THE INVENTION

The present invention relates to an electroanalytic device having an electroanalytical cell and a sample degassing system, and a method for voltammetric analysis of a liquid sample solution.

BACKGROUND OF THE INVENTION

Voltammetry is an electroanalytical method used in analytical chemistry and industrial processes. Voltammetric techniques involve the application of potential to an electrode in an analytical cell and monitoring the resulting current flowing through the cell.

Electroanalytical detectors and voltammetric cells are known in the field and have long been used for the analysis of trace elements in the laboratory. An electroanalytical cell has three electrodes: a working electrode, an auxiliary electrode, and a reference electrode. The working electrode is the electrode where the reaction of interest occurs. The working electrode is either cathodic or anodic depending on whether the reaction is a reduction or oxidation reaction. Working electrodes are sometimes mercury electrodes, but can also be made of other materials, for example inert metals or inert carbon. Auxiliary and reference electrodes are used to establish and maintain a constant potential relative to the working electrode. A current that is equal in magnitude but opposite in charge to the current of the working electrode is passed through the auxiliary electrode. The auxiliary electrode, also known as the counter electrode, prevents undesired current from passing through the reference electrode, and usually consists of a thin platinum wire, gold wire, or any other conductive material that does not affect the sample. The reference electrode is used to measure electroanalytical potential and typically consists of an electrode with a stable and well-known electrode potential, for example a calomel electrode or a silver/silver chloride electrode.

Voltammetric instruments having a working electrode that is a dropping mercury electrode (DME) are known in the art. These classical voltammetric instruments are characterized by a mercury drop formed at the end of a glass capillary tube, the tip of which is exposed to a sample solution. The unique physical properties and surface tension between mercury and the glass capillary tube provide repeatability and stability of the mercury drop, thus providing a simple method for renewing the electrode surface by forming a new drop. However, the DME also has significant drawbacks that limit its use as an automated detector for unattended field use. The primary limitations of the DME are (1) capillary clogging that necessitates frequent capillary replacement; (2) high volume batch cells that are unsuitable for flow-through operation; and (3) large amounts of mercury waste generated during electroanalytical cell operation that trigger health and environmental concerns.

Attempts have been made to improve the classical DME. Barnes et al. in U.S. Pat. No. 4,138,322 describe a degassing system based on a glass degassing chamber. Although the system allows an intense degassing process, it suffers from unsatisfactory gas/fluid separation and a complicated and ineffective electroanalytical cell design. Yarnitsky in WO 99/28,738 describes a regenerated DME that purifies and reuses mercury through contact with oxygenated water. However, despite some adaptation of the system to flow conditions, there are persistent disadvantages related to the use of a glass capillary. Dozortsev in WO 03/019133 describes an electroanalytical cell design that eliminates the glass capillary and provides online mercury purification, however, only samples that have been previously degassed can be analyzed.

Thus, there exists a need for an integrated voltammetric system in which a mercury electrode, a degassing system, and operation of the entire instrument are integrated and adapted to automatic flow operation. The present invention fulfills this need and provides further related advantages.

SUMMARY OF THE INVENTION

In one aspect, the invention provides an electroanalytic device having an electroanalytical cell, a degassing system, and a circulating means. The electroanalytical cell has a working electrode, an auxiliary electrode, and a reference electrode. The degassing system is in fluid communication with the electroanalytical cell. The circulating means is for continuously circulating a sample through the electroanalytical cell and the degassing system.

In one embodiment, the working electrode is a dropless mercury electrode. In another embodiment, the auxiliary electrode is selected from the group consisting of mercury, glassy carbon, platinum, gold, silver, nickel, and palladium. In another embodiment, the reference electrode is selected from the group consisting of silver chloride and calomel.

In one embodiment, the degassing system comprises a degassing chamber. In one embodiment, the degassing system comprises a heat source.

In one aspect, the invention provides a system for voltammetric analysis having a separation chamber, an electroanalytical cell, a flow channel, a degassing system, and a pump. The separation chamber is for receiving and separating a sample/gas mixture. The electroanalytical cell has a flow path with a working electrode inlet, an auxiliary electrode, a reference electrode, and a mercury metal chamber. The flow channel is for providing fluid communication between the separation chamber and the electroanalytical cell. The degassing system is for degassing the liquid sample solution and is in fluid communication with the electroanalytical cell and the separation chamber. The pump is for circulating the liquid sample solution through the separation chamber, the electroanalytical cell, and the degassing system.

In one embodiment, the working electrode is a dropless mercury electrode disposed between the separation chamber and the mercury chamber. In another embodiment, the auxiliary electrode is mercury contained in the mercury chamber. In another embodiment, the reference electrode is disposed within a mercury-free upper portion of the mercury chamber.

In one embodiment, the separation chamber has a first sample inlet for receiving the liquid sample/gas mixture, a sample outlet for dispensing the liquid sample solution into the flow channel, a second sample inlet for receiving a degassed liquid sample solution from the degassing system, and a vent for releasing gas that has been separated from the degassed liquid sample solution.

In one embodiment, the flow channel is disposed between the separation chamber and the mercury chamber. The flow channel is in fluid communication with a mercury channel for supplying mercury to the working electrode.

In one embodiment, the mercury chamber has a mercury chamber inlet for receiving the liquid sample solution and mercury from the flow channel, a first mercury chamber outlet for dispensing the liquid sample solution, and a second mercury chamber outlet for dispensing mercury to a mercury channel.

In one embodiment, the degassing system has a degassing chamber, a degassing inlet for receiving the liquid sample solution and a gas into the degassing chamber, and a degassing outlet for dispensing a degassed liquid sample solution and excess gas into the separation chamber.

In one embodiment, the pump has a pump inlet in communication with the first mercury chamber outlet of the mercury chamber, and a pump outlet in communication with the degassing system.

In one embodiment, a rinse valve is disposed between the first mercury chamber outlet and the pump inlet. In one embodiment, a drain valve is disposed between the pump outlet and the degassing system.

In another aspect, the invention provides a method for voltammetry having the steps of:

(a) introducing a liquid sample solution into an electroanalytical cell of an electroanalytic device, wherein the electroanalytic device also has a degassing system and a pump;

(b) pumping the liquid sample solution through the electroanalytical cell to the degassing system;

(c) introducing an inert gas into the degassing system, thereby causing separation of the dissolved gas (e.g., oxygen, chlorine) from the liquid sample solution and providing a degassed liquid sample solution;

(d) pumping the degassed liquid sample solution into the electroanalytical cell; and (e) making a voltammetric measurement of the degassed liquid sample solution.

In one embodiment, the electroanalytical cell has a working electrode, an auxiliary electrode, and a reference electrode.

In one embodiment, the inert gas is nitrogen, argon, or helium.

In one embodiment, the degassing system has a degassing chamber. In one embodiment, the degassing chamber is a chemically inert material. In one embodiment, the degassing system further comprises a heat source or a UV light source.

In one embodiment, the pump is operated in synchronization with the electroanalytical cell.

In one aspect, the invention provides a method for voltammetric analysis of a liquid sample solution having the steps of:

(a) introducing a liquid sample solution into a separation chamber of an electroanalytical device, wherein the electroanalytical device further comprises a degassing system and an electroanalytical cell;

(b) transferring the liquid sample solution into the degassing system;

(c) introducing an inert gas into the degassing system, wherein the inert gas contacts the liquid sample solution and provides a degassed liquid sample solution;

(d) transferring the degassed liquid sample solution from the degassing system into the separation chamber;

(e) transferring the degassed liquid sample solution from the separation chamber into a flow channel, wherein the flow channel provides fluid communication between the separation chamber and the electroanalytical cell, and wherein a working electrode is disposed within the flow channel; and (f) making a voltammetric measurement of the degassed liquid sample solution.

In one embodiment, the degassed liquid sample solution contains metal ions selected from the group consisting of Cu, Pb, Cd, Zn, Tl, Mn, Ni, Co, Fe, Se, Mo, Ti, Cr, and Sn.

In one embodiment, the working electrode is a dropless mercury electrode and further comprises a platinum wire for providing an electrical current.

In one embodiment, the working electrode has a potential from between +0.3V to −2.2V relative to a reference electrode.

In one embodiment, the degassing system has a degassing chamber with an internal diameter from between 0.2 to 2.0 millimeters.

In one embodiment, the inert gas is nitrogen, argon, or helium.

In one embodiment, transferring the degassed liquid sample solution is done by pumping.

In one embodiment, mercury is transferred from a mercury chamber into the flow channel and forms a mercury meniscus at the working electrode.

In one embodiment, transfer of the degassed liquid sample solution into the flow channel and application of the accumulating potential to the working electrode causes metal ions contained in the degassed liquid sample solution to accumulate on the working electrode.

In one embodiment, making a voltammetric measurement of a degassed liquid sample solution is done by scanning the working electrode.

In one embodiment, after applying a measurement scan to the working electrode, the sample is transferred through the flow channel and into the mercury chamber.

In one embodiment, the sample propels mercury from the working electrode into the mercury chamber.

In one embodiment, the sample is transferred out of the mercury chamber and discarded through a drain valve.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

Figure 1:
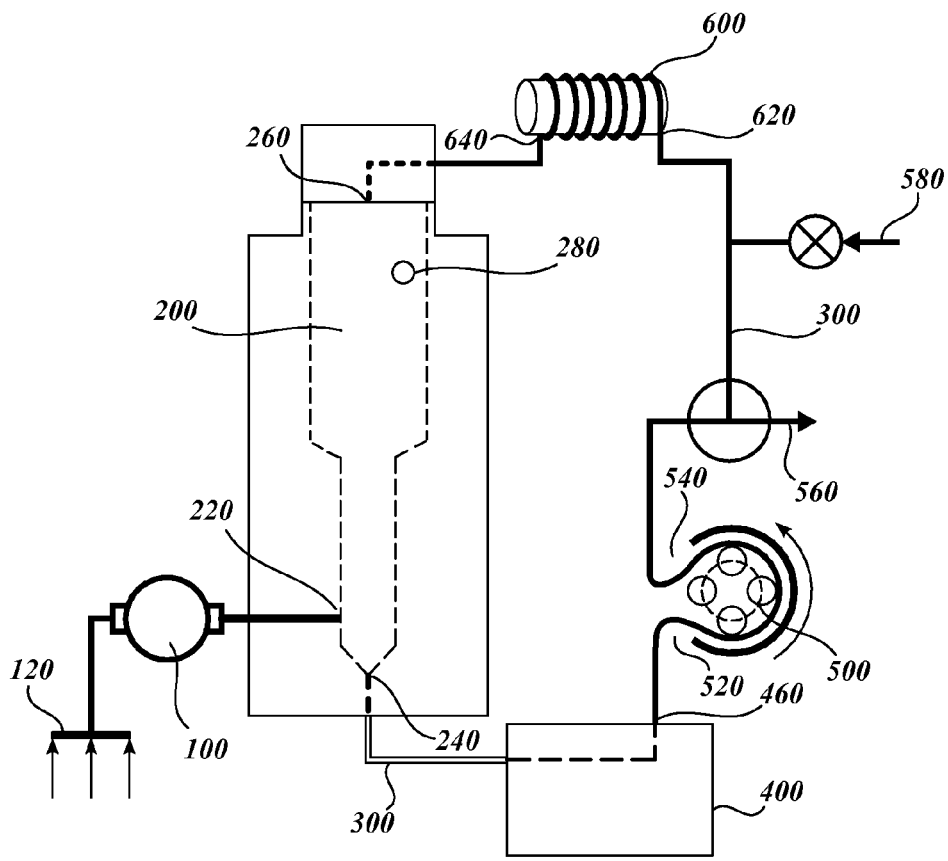
FIG. 1 is a schematic illustration of a representative system of the invention for voltammetric analysis that includes an electroanalytical cell and degassing system.

The present invention provides an electroanalytic device having an electroanalytical cell and a degassing system, and a method for voltammetric analysis of a liquid sample solution using the electroanalytical device. In one embodiment, the electroanalytical cell includes a dropless mercury electrode (e.g., mercury meniscus electrode).

The electroanalytic device and voltammetric analysis method are useful for voltammetric analysis of a liquid sample solution containing trace metals. The device and method are also useful for degassing and screening liquid sample solutions without the need for a separate degassing system.

The liquid sample solution includes the liquid sample of interest. The liquid sample includes one or more metal ions. In addition, the liquid sample solution may also include buffers, electrolytes, chelating agents, and/or calibration standards. Buffer solutions include, without limitation, ammonia or acetate (e.g., 0.1 M). Chelating agents include, without limitation, dimethylglyoxime (DMG), diethylenetriaminepentaacetic acid (DTPA), or oxine. Calibration standards are solutions containing known quantities of metal ions.

In one embodiment, the invention provides an electroanalytic device having an electroanalytical cell, a degassing system, and a circulating means. The electroanalytical cell has a working electrode, an auxiliary electrode, and a reference electrode. The working electrode can be any metal alloy that is liquid at room temperature, for example, mercury or gallium. In one embodiment of the electroanalytic device, the working electrode is a dropless mercury electrode. The classical glass capillary used for mercury drop formation is eliminated in this embodiment. Elimination of the glass capillary contributes to higher overall system robustness, stability, and safety. The dropless mercury electrode is well suited for inflow operation, whereby formation of the dropless mercury electrode, sample mixing/degassing, and accumulating stages are flow assisted and can be easily synchronized and/or paralleled. Moreover, the dropless mercury electrode is mechanically stable and has a virtually unlimited lifetime. As a result, high sample flow rates and long accumulating times can be used. In addition, the analytical capabilities of the electrode are expanded due to the possibility of applying broader negative scans.

The auxiliary electrode is selected from mercury, glassy carbon, platinum, or gold electrodes. In one embodiment, the auxiliary electrode is mercury. The reference electrode is selected from silver/silver chloride or calomel electrodes. In one embodiment, the reference electrode is a silver/silver chloride electrode.

The system of the invention advantageously includes a degassing system. The degassing system is in fluid communication with the electroanalytical cell, and is highly effective, versatile, and capable of rapid removal of a variety of dissolved gasses from the liquid sample introduced into the device of the invention. In one embodiment, the degassing system has a degassing chamber. In one embodiment, the degassing chamber is a tube. The tube may be a straight tube or a coiled or serpentine tube. The degassing chamber is useful for producing turbulence in the liquid sample solution. Turbulence aids both in mixing the liquid sample solution and in separating dissolved gases such as oxygen and carbon dioxide from the solution (degassing). In one embodiment, the degassing chamber is made of a chemically inert material. For example, the degassing chamber can be made of TEFLON or PEEK plastic, however, other chemically inert materials can also be used.

In one embodiment, the degassing system includes a heat source. Heating the liquid sample solution is useful for removal of gases other than oxygen. For example, heating the liquid sample solution is useful for the removal of chlorine gas.

The entire electroanalytic device, including the electroanalytical cell and the degassing system, can be miniaturized and combined into a single, chemically-inert plastic device that is free of moving parts. The miniaturized, chemically-inert design is economical and effective due to its high sample throughput and reduction of both sample and reagent volumes. For example, in one embodiment the total amount of mercury used is 200 μl or less. In comparison, a classical DME not only consumes mercury, but also lacks the capacity for mercury purification and generates mercury waste.

In one embodiment, the invention provides a system for voltammetric analysis having a separation chamber, an electroanalytical cell, a flow channel, a degassing system, and a pump. The separation chamber receives a liquid sample solution. The electroanalytical cell has a working electrode, an auxiliary electrode, a reference electrode, and a mercury chamber. The flow channel provides fluid communication between the separation chamber and the electroanalytical cell. The degassing system degasses the liquid sample solution, and is in fluid communication with the electroanalytical cell and the separation chamber. The pump circulates the liquid sample solution through the separation chamber, the electroanalytical cell, and the degassing system.

In one embodiment of the system, the working electrode is a dropless mercury electrode disposed between the separation chamber and the mercury chamber. In one embodiment, the auxiliary electrode comprises mercury contained in the mercury chamber. In one embodiment, the reference electrode is disposed within a mercury-free upper portion of the mercury chamber.

In one embodiment of the system, the separation chamber has a first sample inlet for receiving the liquid sample solution, a sample outlet for dispensing the liquid sample solution into the flow channel, a second sample inlet for receiving a degassed liquid sample solution from the degassing system, and a vent for releasing gas that has been separated from the degassed liquid sample solution.

In one embodiment of the system, the flow channel is disposed between the separation chamber and the mercury chamber. The flow channel is in fluid communication with a mercury channel for supplying mercury to the working electrode.

In one embodiment of the system, the mercury chamber has a mercury chamber inlet for receiving the liquid sample solution and mercury from the flow channel, a first mercury chamber outlet for dispensing the liquid sample solution, and a second mercury chamber outlet for dispensing mercury to a mercury channel.

In one embodiment of the system, the degassing system has a degassing chamber, a degassing inlet for receiving the liquid sample solution and a gas into the degassing chamber, and a degassing outlet for dispensing a degassed liquid sample solution and excess gas into the separation chamber.

In one embodiment of the system, the pump has a pump inlet in communication with the first mercury chamber outlet of the mercury chamber, and a pump outlet in communication with the degassing system.

In embodiment, a rinse valve is disposed between the first mercury chamber outlet and the pump inlet. In one embodiment, a drain valve is disposed between the pump outlet and the degassing system.

Figure 2:
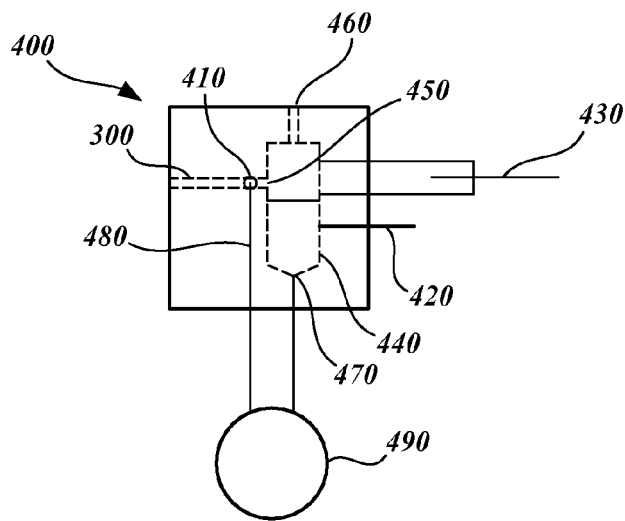
FIG. 2 is a schematic illustration of a representative electroanalytical cell useful in the system of the invention.

A representative system for voltammetric analysis of the invention is shown in FIG. 1. The system is essentially a loop that includes a separation chamber 200, a flow channel 300, an electroanalytical cell 400, a circulation pump 500, and a degassing system 600. A detailed illustration of the electroanalytical cell 400 is shown in FIG. 2. Referring to FIG. 2, representative electroanalytical cell 400 includes a working electrode 410, an auxiliary electrode 420, a reference electrode 430, and a mercury chamber 440.

Referring to FIGS. 1 and 2, the system has two vertically drilled chambers, separation chamber 200 and mercury chamber 440. The separation chamber 200 is generally larger than the mercury chamber 440, and includes a first sample inlet 220, a sample outlet 240, and a second sample inlet 260. The mercury chamber 440 includes a mercury chamber inlet 450, a first mercury chamber outlet 460, and a second mercury chamber outlet 470. The separation chamber 200 and the mercury chamber 440 are connected with each other by a horizontally drilled flow channel 300. A mercury channel 480 is drilled perpendicularly to the flow channel 300 between the separation chamber 200 and the mercury chamber inlet 450 of the mercury chamber 440.

The system has a mercury pump 490 for transferring mercury from the mercury chamber 440 through the mercury channel 480 to the working electrode 410. In one embodiment, the mercury pump 490 is a peristaltic pump. The reference electrode 430 is positioned in the upper part of the mercury chamber 440 above the mercury level. The auxiliary electrode 420 is positioned within the mercury chamber 440. In one embodiment, the surface of the mercury contained within the mercury chamber 440 serves as the auxiliary electrode 420.

The system has a circulation pump 500. The circulation pump 500 includes a circulation pump inlet 520 and a circulation pump outlet 540. The circulation pump inlet 520 is in fluid communication with the first mercury chamber outlet 460 of the mercury chamber 440. The circulation pump outlet 540 is in fluid communication with the gas inlet 580 and the degassing chamber 600.

The degassing chamber 600 includes a degassing chamber inlet 620 and a degassing chamber outlet 640. The degassing chamber outlet 640 is in fluid communication with the second sample inlet 260 of the separating chamber 200. The second sample inlet 260 is above the fluid level in the separating chamber 200. A vent 280 is positioned in the upper part of the sample chamber 200, above the level of the liquid sample solution.

In one embodiment, the invention provides a method for voltammetry. The method includes the following steps:

(a) introducing a liquid sample solution into an electroanalytical cell of an electroanalytic device, wherein the electroanalytic device also has a degassing system and a pump;

(b) pumping the liquid sample solution through the electroanalytical cell to the degassing system;

(c) introducing an inert gas into the degassing system, thereby causing separation of the dissolved gas from the liquid sample solution and providing a degassed liquid sample solution;

(d) pumping the degassed liquid sample solution into the electroanalytical cell; and (e) making a voltammetric measurement of the degassed liquid sample solution.

In one embodiment, the electroanalytical cell has a working electrode, an auxiliary electrode, and a reference electrode.

In one embodiment, the inert gas is nitrogen, argon, or helium.

In one embodiment, the degassing system has a degassing chamber. In one embodiment, the degassing system further comprises a heat source and/or a UV light source. A UV light source is useful for eliminating bacteria and other pathogens from a liquid sample solution.

In one embodiment, the pump is operated in synchronization with the electroanalytical cell. Operation of the pump is described in more detail, below.

In one aspect, the invention provides a method for voltammetric analysis of a liquid sample solution. The method includes the following steps:

(a) introducing a liquid sample solution into a separation chamber of an electroanalytical device, wherein the electroanalytical device further comprises a degassing system and an electroanalytical cell;

(b) transferring the liquid sample solution into the degassing system;

(c) introducing an inert gas into the degassing system, wherein the inert gas contacts the liquid sample solution and provides a degassed liquid sample solution;

(d) transferring the degassed liquid sample solution from the degassing system into the separation chamber;

(e) transferring the degassed liquid sample solution from the separation chamber into a flow channel, wherein the flow channel provides fluid communication between the separation chamber and the electroanalytical cell, and wherein a working electrode is disposed within the flow channel; and (f) making a voltammetric measurement of the degassed liquid sample solution.

In one embodiment, the degassed liquid sample solution contains metal ions selected from Cu, Pb, Cd, Zn, Tl, Mn, Ni, Co, Fe, Se, Mo, Ti, Cr, and Sn.

In one embodiment, the working electrode is a dropless mercury electrode and also has a platinum wire for providing an electrical current. In one embodiment, the working electrode has a potential from between +0.3V to −2.2V relative to a reference electrode.

In one embodiment, the degassing system has a degassing chamber with an internal diameter from between 0.2 to 2.0 millimeters.

In one embodiment, the inert gas is nitrogen, argon, or helium.

In one embodiment, transferring the degassed liquid sample solution is done by pumping the degassed liquid sample solution.

In one embodiment, mercury is transferred from a mercury chamber into the flow channel and forms a mercury meniscus at the working electrode.

In one embodiment, transfer of the degassed liquid sample solution into the flow channel and application of the accumulating potential to the working electrode causes metal ions contained in the degassed liquid sample solution to accumulate on the working electrode.

In one embodiment, making a voltammetric measurement of a degassed liquid sample solution is done by scanning the working electrode. Scanning the working electrode means applying a measurement scan to the working electrode.

In one embodiment, after applying a measurement scan to the working electrode, the sample is transferred through the flow channel and into the mercury chamber.

In one embodiment, the sample propels mercury from the working electrode into the mercury chamber.

In one embodiment, the sample is transferred out of the mercury chamber and discarded through the drain valve.

Referring to FIGS. 1 and 2, a representative method of the invention is as follows. Although the method is described in terms of stages, including the sample mixing/degassing stage, the electrode formation stage, the accumulating/measuring stage, and the rinse stage, the stages are synchronized with each other and occur in parallel.

Sample Mixing/Degassing Stage

A sample solution is introduced through chemical manifold 120 into the separation chamber 200 using the chemical pump 100. The sample solution includes the sample to be tested, as well as any additional electrolyte and/or buffer solutions. Once the sample solution has been introduced, the circulation pump 500 begins to circulate the sample solution in a loop through the separation chamber 200, the flow channel 300, the mercury chamber 440, the circulation pump 500, and the degassing chamber 600. In parallel, an inert gas enters the degassing chamber 600 through the gas inlet 580. Any inert gas may be used, for example, nitrogen, helium, or argon. In one embodiment, the inert gas is nitrogen gas. The inert gas forms a turbulent gas and fluid mixture within the degassing chamber. The turbulence mixes the sample solution. Dissolved gasses in the liquid sample are removed from the sample solution, providing a degassed sample solution. The degassed sample solution then enters the upper part of the separation chamber 200, where the gas and fluid mixture is separated; fluid accumulates in the lower part of the separation chamber 200, and gas is exhausted through the vent 280. The amount of fluid present in the separation chamber 200 is typically about 2-5 ml, including the sample, buffers, electrolytes, chelating agents, and calibration standards, collectively referred to as the liquid sample solution.

The length of time required for the sample mixing/degassing stage depends upon the rate that the liquid sample solution is pumped through the system. For example, a 5 ml sample solution pumped through the system at 5 ml/min would take approximately 1 minute to degas; the same sample pumped through the system at 20 ml/min would take approximately 15 seconds to degas. In one embodiment, the pump flow rate is between 10-20 ml/min. At this rate, a 5 ml sample would be degassed in approximately 15-30 seconds, and would circulate through the degassing system about 2-4 times. The degassing chamber length and pump flow rate can be optimized for different applications.

Electrode Formation Stage

As the mixing/degassing stage is completed, both the circulation pump 500 and gas flow through the gas inlet 580 are terminated. The mercury pump 490 is activated, and mercury is delivered from the mercury chamber 440 through the mercury channel 480 into the flow channel 300 where it forms a semi-sphere (e.g., meniscus) due to high mercury surface tension. The timing of the mercury pump 490 is preset so that it stops pumping once the flow channel 300 is completely blocked by the mercury semi-sphere. Generally, an accumulation of 1-3 μl of mercury from the mercury chamber 440 is sufficient to block the flow channel 300. The mercury semi-sphere formed at the junction of the mercury channel 480 and the flow channel 300 is the working electrode 410. Once the accumulating/measuring stage is complete, the circulation pump 500 is activated and sample solution flow propels the mercury semi-sphere through the mercury chamber inlet 450 and into the mercury chamber 440, where it is trapped.

Accumulating/Measuring Stage

Application of the accumulating potential to the working electrode 410 is coordinated with the operation of the circulation pump 500 so that the accumulating stage begins simultaneously with the formation of the working electrode 410. Additional sample solution degassing as described above in the mixing/degassing stage occurs during the accumulating stage, so that the degassing and accumulating stages occur in parallel. As the accumulating stage is completed, the measurement scan is applied to the working electrode 410 and data are recorded. Each time that a new measurement is initiated, a new working electrode 410 is formed by repeating the Electrode Formation Stage described above.

Rinse Stage

Following the measurement stage, the sample solution is released from the system via a drain valve 560 and a rinse solution is fed into the system via rinse valve (not shown). The rinse valve is generally disposed between the first mercury chamber outlet 460 and the pump inlet 520.

All of the stages, including the sample mixing/degassing stage, the electrode formation stage, the accumulating/measuring stage, and the rinse stage are flow-assisted by the circulation pump 500 and can be easily paralleled.

Some metals form amalgams with mercury following application of the measurement scan. The contaminated mercury can be cleaned by applying a positive potential to the mercury surface following the measurement scan.

Depending on the metal concentration in the sample solution and the particular application, different measurement techniques can be used. For example, direct voltammetry (DV) is useful for high metal concentrations, and AdSV is useful for low metal concentrations. These techniques can be used with a variety of calibration methods including a standard calibration curve, the method of standard additions (MSA), or the use of an internal standard. A standard calibration curve is obtained using standard solutions with known concentration of metal ions. Each standard is run separately before the sample is analyzed. The MSA involves preparing "spiked" samples by adding known concentrations of metal ions to the sample solution. Multiple runs are required to analyze the sample at different spiked concentrations. The use of internal standards simplifies the analytical protocol by eliminating the need for external standards, standard additions, or multiple runs.

Approximately 75-80% of known metals can be detected and quantified using the voltammetric system described herein, including all transitional metals; light metals including aluminum, magnesium, calcium, sodium, and potassium; and lanthanides. Commonly measured metals include copper, nickel, cobalt, zinc, lead, cadmium, and tin. Non-metals such as organic surfactants can also be detected and measured. The concentration of up to four different ions can be measured at one time.

The following definitions are provided.

"Working electrode" refers to the place where the reaction of interest occurs. In one embodiment, the working electrode is a dropless mercury electrode that is reproduced prior to each test.

"Auxiliary electrode" or "counter electrode" refers to an electrode paired with a working electrode, through which a current equal in magnitude and opposite in sign to the current passing through the working electrode is passed. The auxiliary electrode can be made, for example without limitation, of metals such as platinum, carbon-based materials, or of any other conductive material that is not affected by the sample solution.

"Reference electrode" refers to a specially designed electrode that maintains a constant potential in reference to a sample solution throughout the measurement cycle. In one embodiment, the reference electrode is a silver/silver chloride electrode. Silver/silver chloride electrodes are available from Ercon, Inc. of Wareham, Mass.; Metech International, Inc. of Worcester, Mass.; and E.I. du Pont de Nemours and Co. of Wilmington, Del.

"Trace element detection" refers to applying an electrical potential between the working electrode and the reference electrode and measuring the resulting current. The resulting current is a function of the concentration of the trace elements in the sample. In one embodiment, the potential of the working electrode ranges from +0.2 to −1.6V in relation to the silver/silver chloride reference electrode, which is about 0.2V versus a normal hydrogen electrode.

The following examples are provided for the purposes of illustrating, not limiting, the invention.

EXAMPLES

Example 1

System Sensitivity and Selectivity

Figure 3:
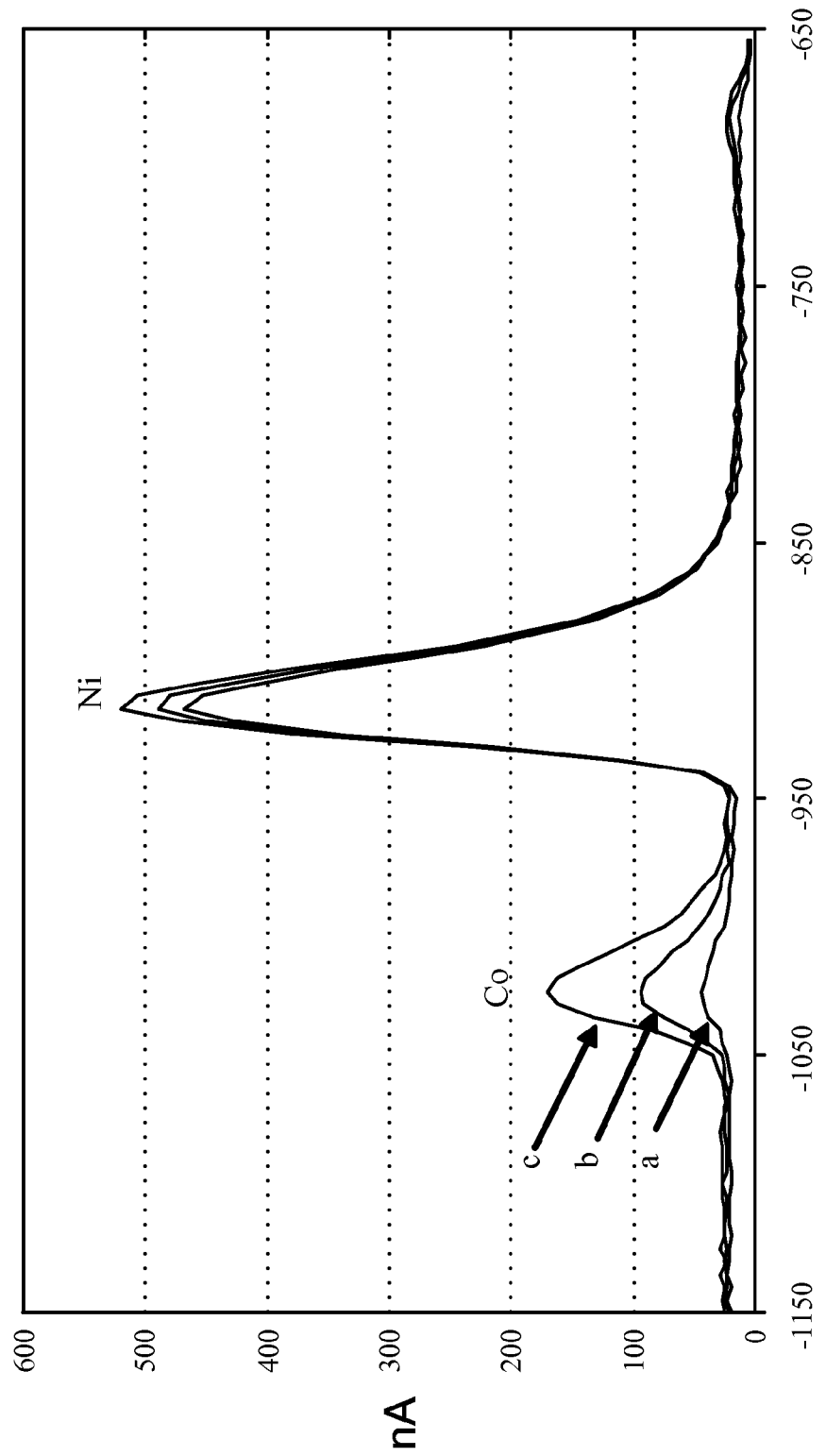
FIG. 3 is a voltammogram showing the detection of ultratrace levels of cobalt in the presence of an excess of nickel.

The sensitivity and selectivity of a representative system and method for voltammetric analysis was demonstrated using AdSV to quantify ultra-trace amounts of cobalt in a sample solution containing a high excess of nickel ions. The MSA was used to determine the cobalt concentration in a blank sample solution of DI water containing 0.1 M buffer ammonia, DMG, and approximately 0.7 µg/L nickel. An accumulation time of 80 seconds was used. FIG. 3 is a voltammogram showing cobalt concentrations in the blank sample (a) and two successive additions (b and c). The blank sample had a cobalt background concentration ranging from 54-73 ng/L. In FIG. 3, the X-axis represents the potential versus Ag/AgCl (mV), and the Y-axis represents current (nA). The method for voltammetric analysis is therefore characterized by high selectivity and high sensitivity, or about 6 nA/ppb·s.

Example 2

Linear Dynamic Range

Figure 4:
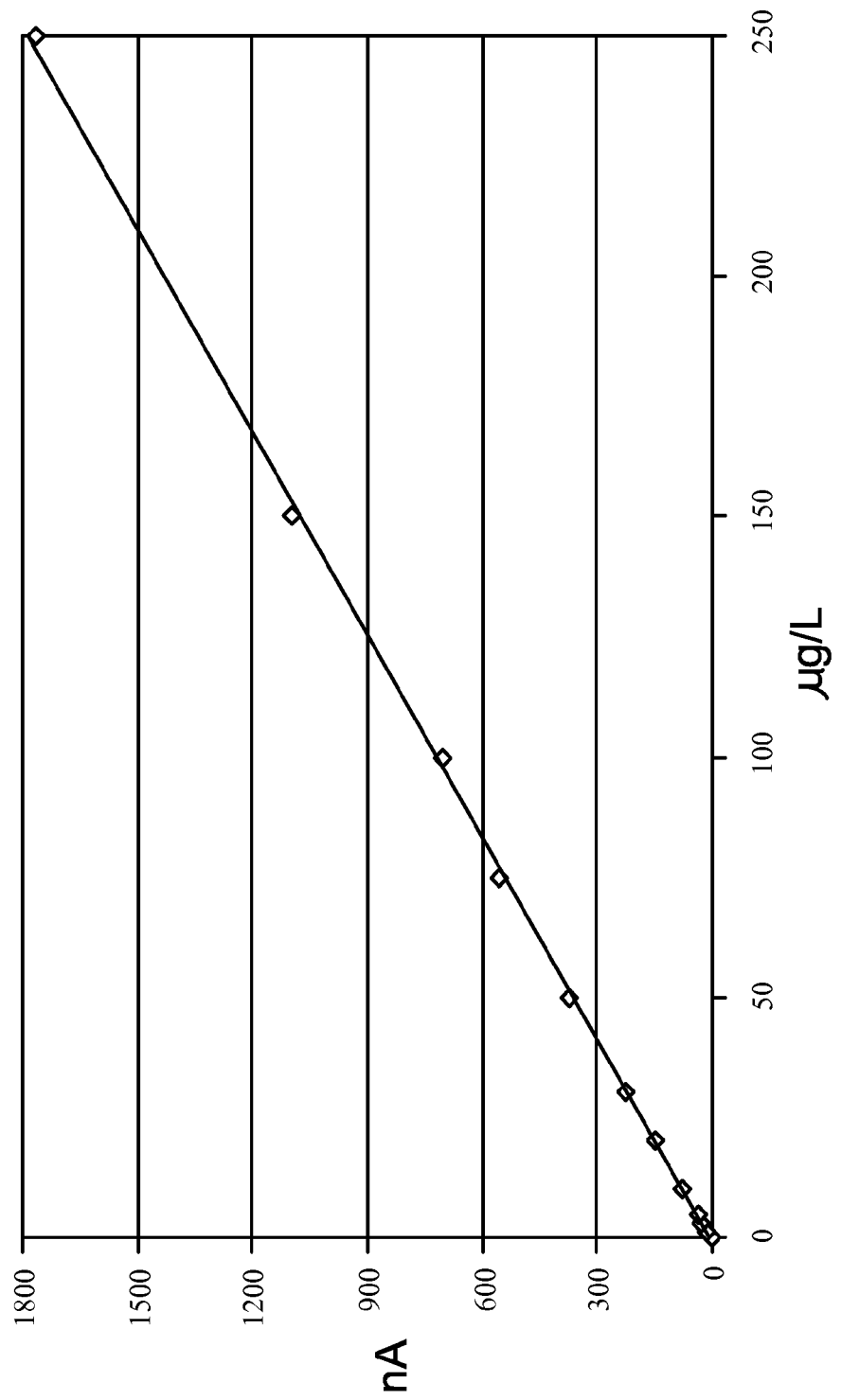
FIG. 4 is a graph of a calibration curve obtained by a representative device and method of the invention using adsorptive stripping voltammetry (AdSV) to measure varying concentrations of cobalt in solution.

The response over a wide concentration range of a representative voltammetric system was evaluated by constructing calibration curves in solutions with varying concentrations of analyte. The ability of the system to respond linearly to low (on the order of parts per billion, or ppb) and high (on the order of parts per million, or ppm) concentrations of analyte was evaluated using AdSV. A representative cobalt calibration curve is shown in FIG. 4. The cobalt calibration curve was obtained using synthetic DI water samples containing 0.1 M buffer ammonia, DMG, and test spikes of 1.0-250 µg/L cobalt. In FIG. 4, the X-axis represents cobalt concentration (µg/L); the Y-axis represents current (nA); and $R^2$ is equal to 0.9995.

Figure 5:
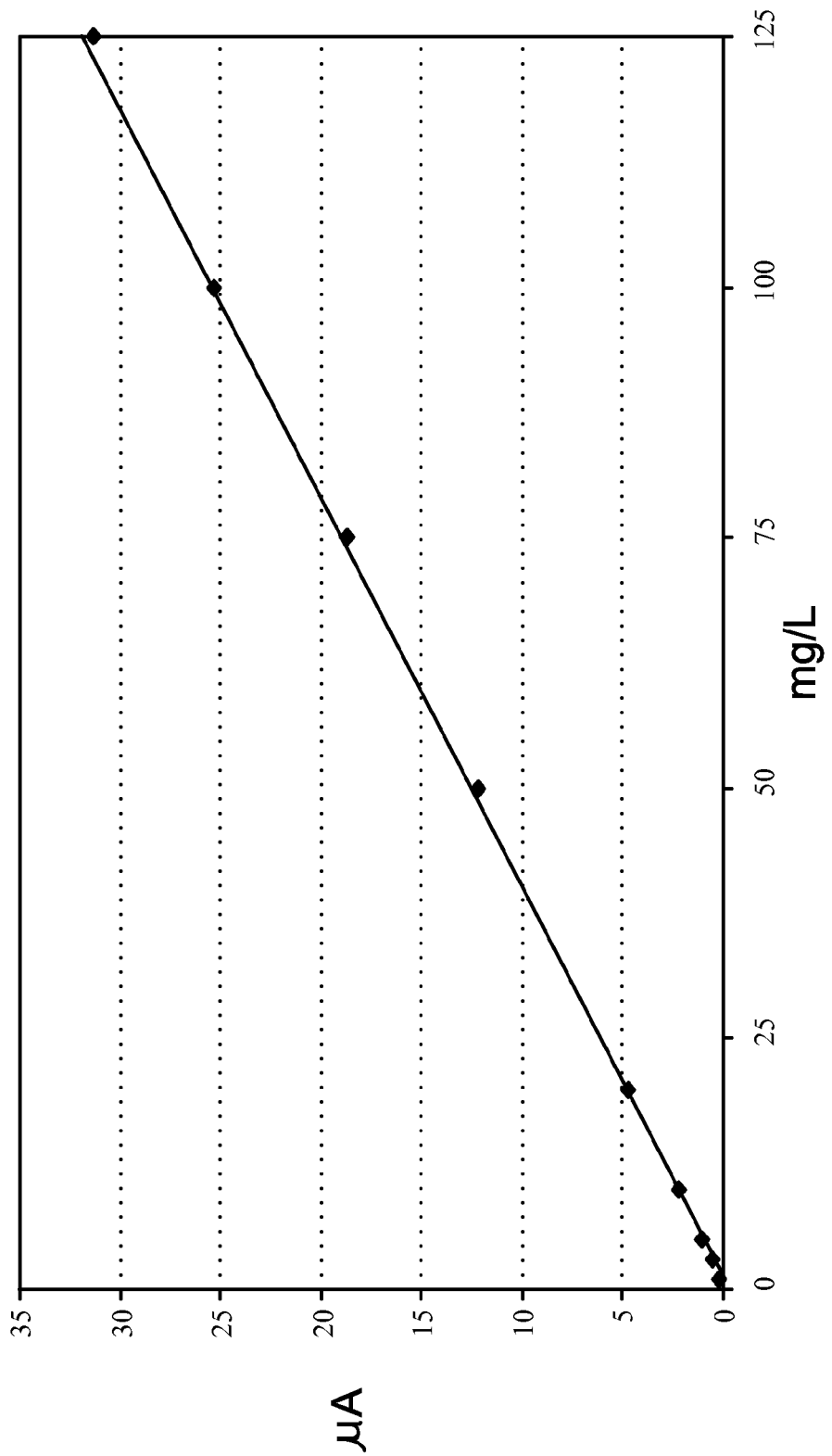
FIG. 5 is a graph of a calibration curve obtained by a representative device and method of the invention using direct square wave (SW) voltammetry to measure varying concentrations of copper in solution.

The ability of the system to respond to high (ppm) concentrations of analyte was evaluated using direct SW voltammetry. A representative copper calibration curve is shown in FIG. 5. The copper calibration curve was obtained using synthetic DI water samples containing 0.1 M nitric acid and test spikes of 1.0-125 mg/L copper. In FIG. 5, the X-axis represents copper concentration (mg/L); the Y-axis represents current (µA); and $R^2$ is equal to 0.9992. The calibration curves shown in FIGS. 4 and 5 illustrate the linear response observed in concentration ranges covering two orders of magnitude. Both low and high concentration ranges can therefore be measured without any changes in the design of the voltammetric system of the present invention.

Example 3

Accuracy and Precision

Figure 6:
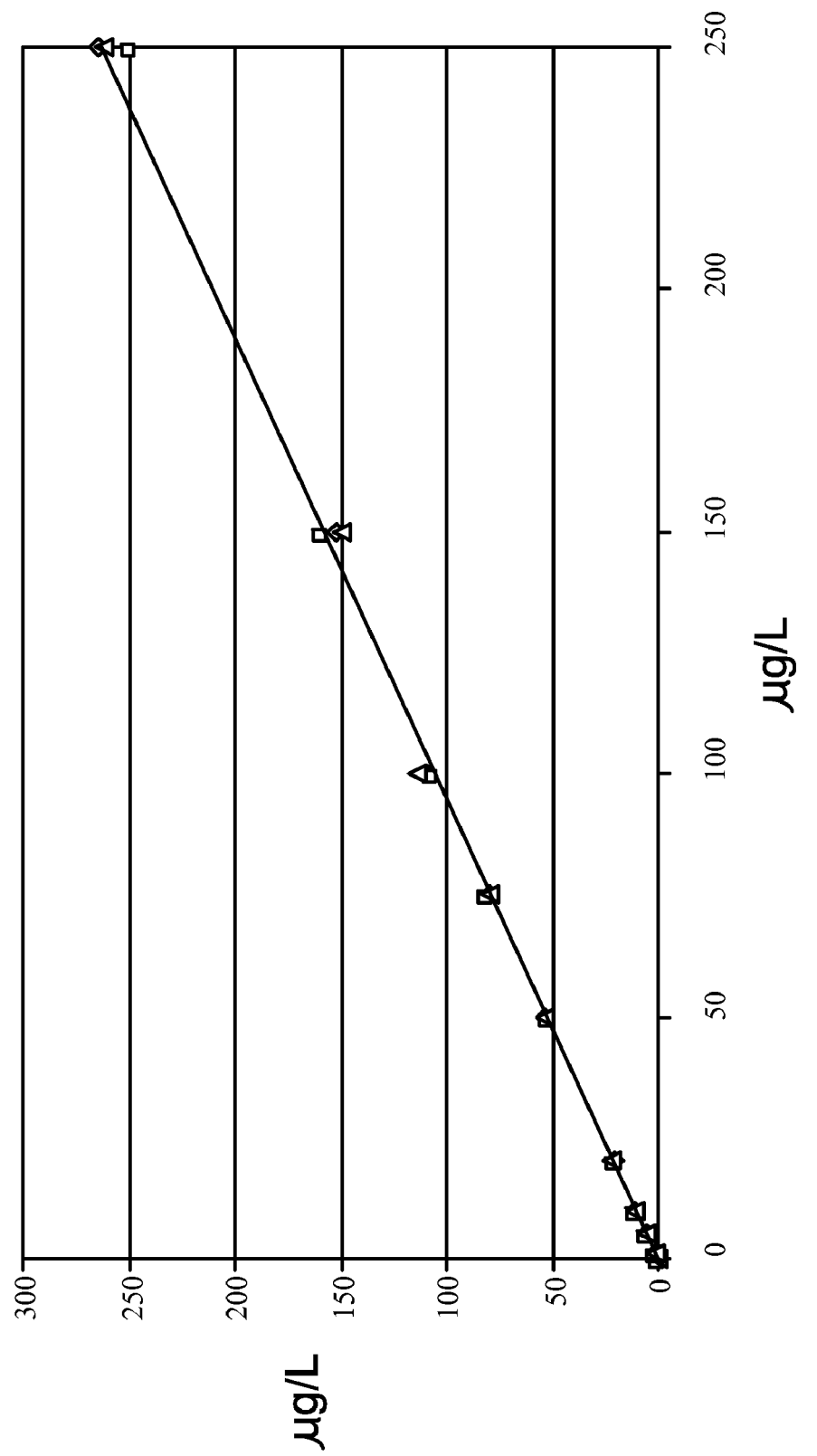
FIG. 6 is a graph showing the concentration of cobalt in spiked deionized (DI) water samples determined by a representative device and method of the invention.

The analytical performance of a representative voltammetric system was evaluated by measuring not only synthetic test solutions but also real spiked samples. The cobalt concentration of spiked DI water samples containing 0.1 M buffer ammonia, DMG, and test spikes of 1.0-250 µg/L cobalt was determined using AdSV. FIG. 6 is a voltammogram showing the cobalt concentration measured in three separate trials. In FIG. 6, the X-axis represents the amount of added cobalt (µg/L); the Y-axis represents the amount of cobalt detected (µg/L); y is equal to 1.0519x+0.0507; and $R^2$ is equal to 0.9992. The data from the three trials are represented by diamonds (Trial 1); triangles (Trial 2); and squares (Trial 3). Table 1 shows the amount of cobalt added (µg/L) and the amount of cobalt found (µg/L) for each of the three trials corresponding to FIG. 6.

TABLE 1

| Cobalt Added | Cobalt Found, Trial 1 | Cobalt Found, Trial 2 | Cobalt Found, Trial 3 |
| --- | --- | --- | --- |
| 1 | 1.5 | 1.53 | 1.45 |
| 5 | 5.65 | 4.92 | 5.18 |
| 10 | 10.5 | 11.1 | 10.8 |
| 30 | 29.9 | 31.9 | 34.7 |
| 50 | 52.8 | 51.5 | 54 |
| 100 | 109 | 110 | 107 |
| 150 | 158 | 143 | 149 |
| 250 | 265 | 262 | 250 |

Figure 7:
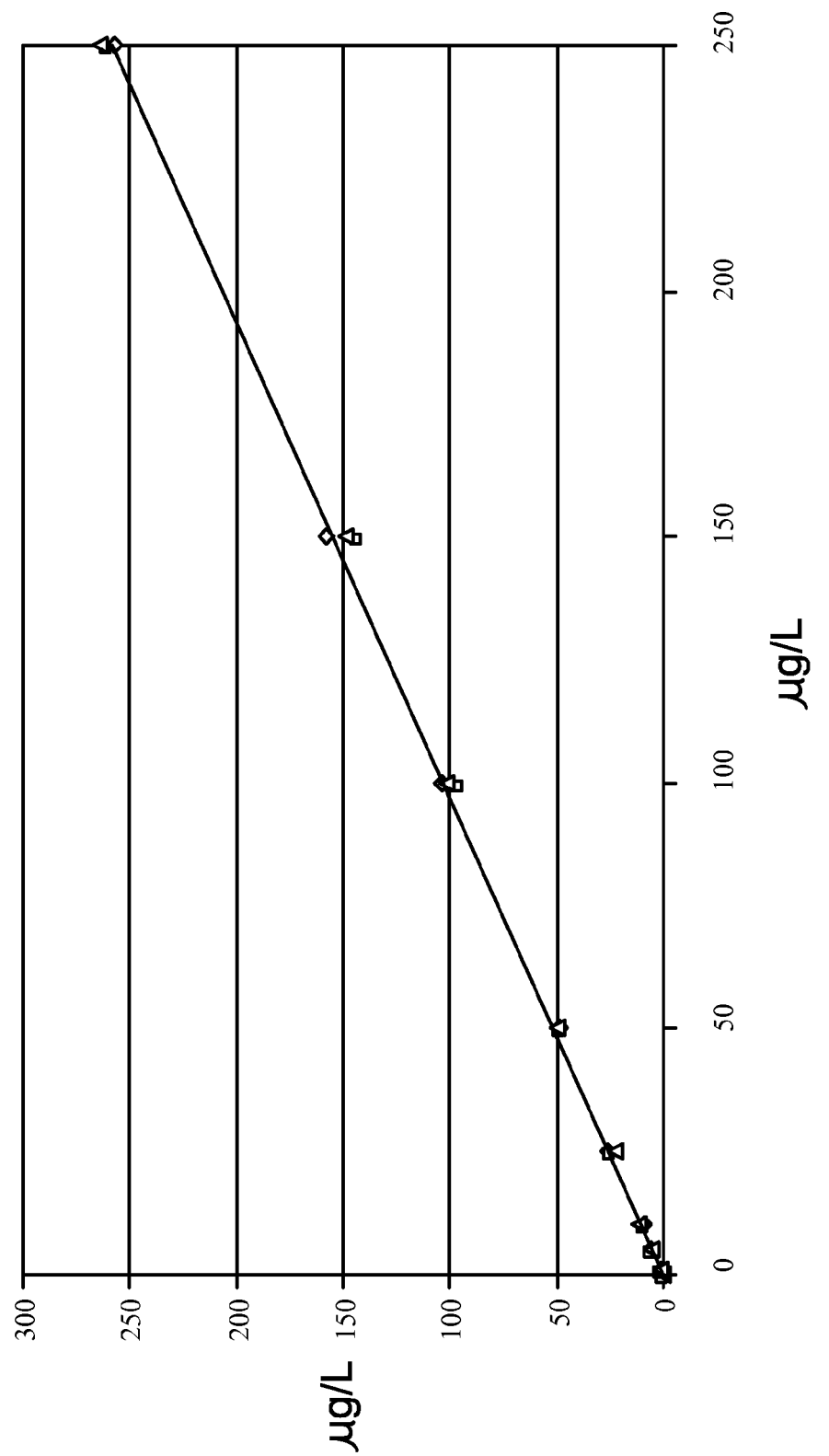
FIG. 7 is a graph showing the concentration of nickel in spiked DI water samples determined by a representative device and method of the invention.

The nickel concentration of spiked DI water samples containing 0.1 M buffer ammonia, DMG, and test spikes of 1.0-250 µg/L nickel was determined using AdSV. FIG. 7 is a voltammogram showing the nickel concentration measured in three separate trials. In FIG. 7, the X-axis represents the amount of added nickel (µg/L); the Y-axis represents the amount of nickel detected (µg/L); y is equal to 1.0346x−0.1935; and $R^2$ is equal to 0.9996. The data from the three trials are represented by diamonds (Trial 1); squares (Trial 2); and triangles (Trial 3). Table 2 shows the amount of nickel added (µg/L) and the amount of nickel found (µg/L) for each of the three trials corresponding to FIG. 7.

TABLE 2

| Nickel Added | Nickel Found, Trial 1 | Nickel Found, Trial 2 | Nickel Found, Trial 3 |
| --- | --- | --- | --- |
| 0 | 0.38 | 0.408 | 0.409 |
| 1 | 1.29 | 1.39 | 1.26 |
| 5 | 5.41 | 5.53 | 5.59 |
| 10 | 9.33 | 9.49 | 11.8 |
| 25 | 26 | 25.1 | 22.9 |
| 50 | 48.3 | 48.1 | 50.1 |
| 100 | 104 | 96 | 101 |

TABLE 2-continued

| Nickel Added | Nickel Found, Trial 1 | Nickel Found, Trial 2 | Nickel Found, Trial 3 |
|---|---|---|---|
| 150 | 158 | 143 | 149 |
| 250 | 257 | 261 | 264 |

Based on the data presented in FIGS. 6 and 7 and Tables 1 and 2, both cobalt and nickel concentrations can be determined using AdSV with the accuracy and precision of 1 µg/L or ±10% (whichever is larger) in concentrations ranging from 1.0-250 µg/L.

Figure 8:
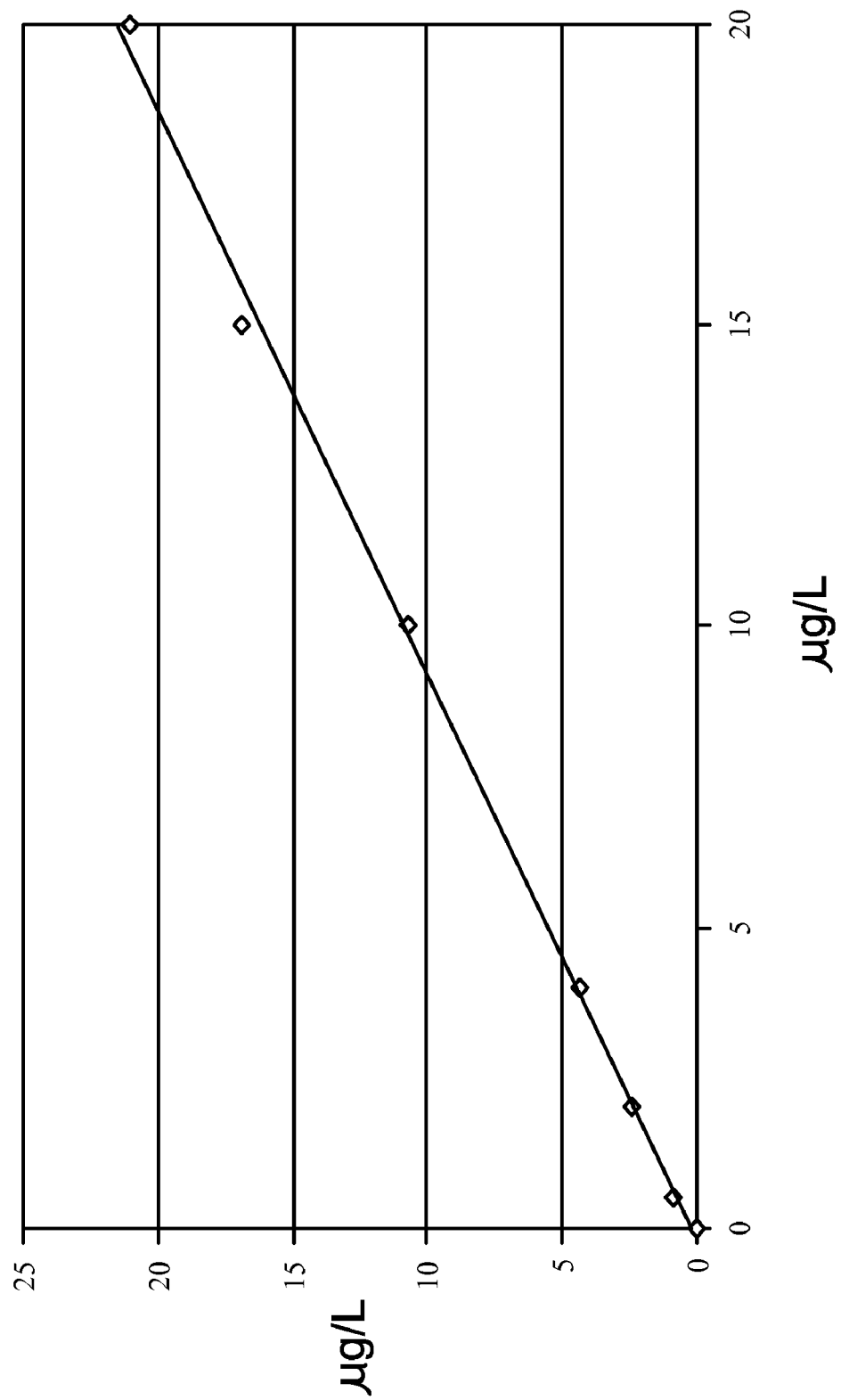
FIG. 8 is a graph showing the concentration of chromium in spiked DI water samples determined by a representative device and method of the invention.

The chromium concentration of spiked DI water samples containing buffer acetate (pH 6.0), DTPA, and test spikes of 0.5-20 µg/L Cr(VI) was determined using AdSV. FIG. 8 is a voltammogram showing the amount of chromium in spiked samples. In FIG. 8, the X-axis represents the amount of added chromium (µg/L); the Y-axis represents the amount of chromium detected (µg/L); y is equal to $1.0649x+0.2037$; and $R^2$ is equal to 0.998. Based on the data presented in FIG. 8, chromium(VI) can be determined using AdSV with the accuracy and precision of 0.5 µg/L or ±10% (whichever is larger) in concentrations ranging from 0.5-20 µg/L. Pre-oxidizing the sample solution with permanganate prior to measurement permits the determination of total chromium (speciation).

Figure 9:
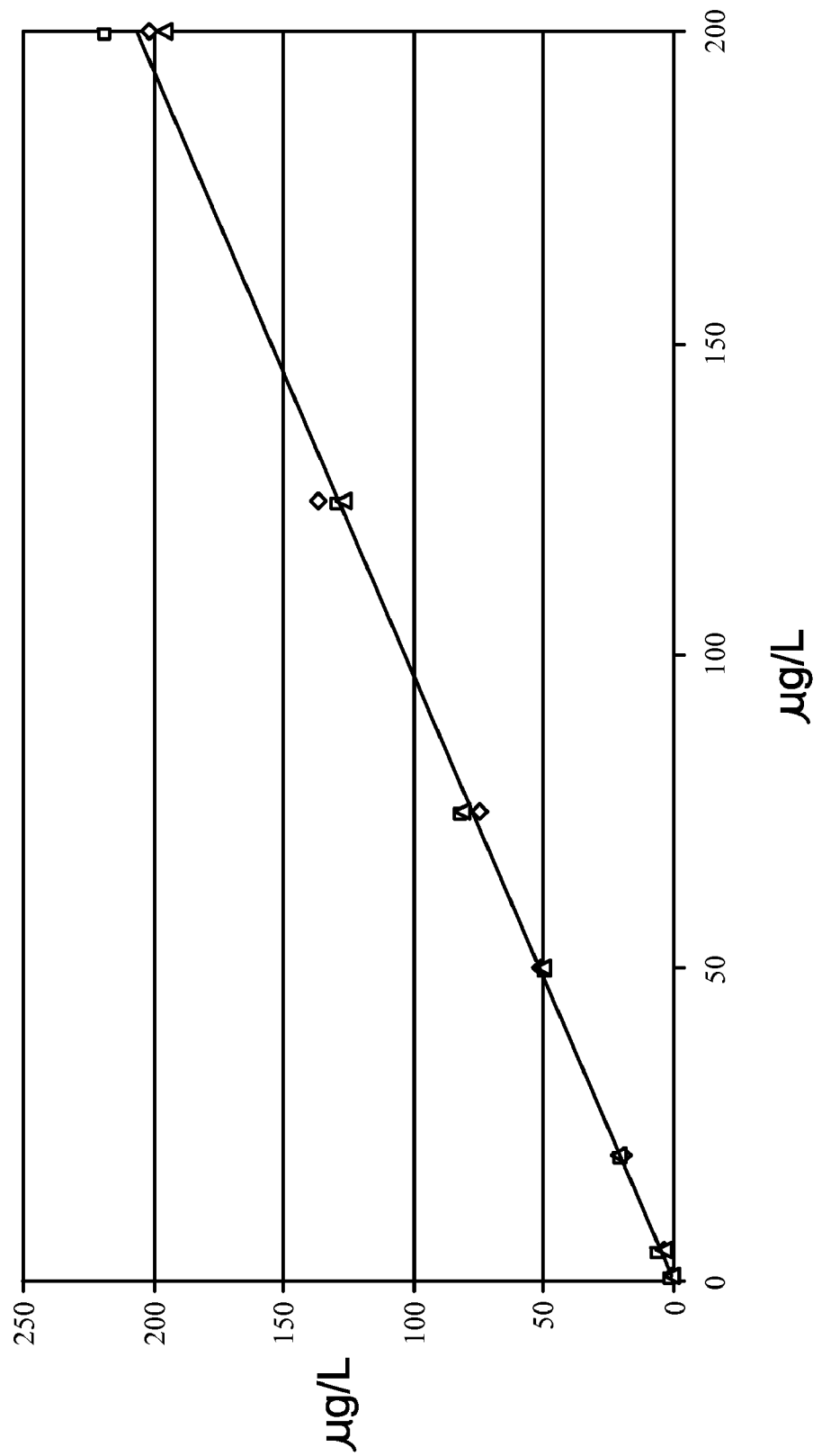
FIG. 9 is a graph showing the concentration of copper in spiked DI water samples determined by a representative device and method of the invention.

The copper concentration of spiked DI water samples containing 0.1 M buffer ammonia, oxine, and test spikes of 1.0-200 µg/L copper was determined using AdSV. FIG. 9 is a voltammogram showing the copper concentration measured in three separate trials. In FIG. 9, the X-axis represents the amount of added copper (µg/L); the Y-axis represents the amount of copper detected (µg/L); y is equal to $1.0317x-0.2297$; and $R^2$ is equal to 0.9972. The data from the three trials are represented by diamonds (Trial 1); squares (Trial 2); and triangles (Trial 3). Table 3 shows the amount of copper added (µg/L) and the amount of copper found (µg/L) for each of the three trials corresponding to FIG. 9.

TABLE 3

| Copper Added | Copper Found Trial 1 | Copper Found Trial 2 | Copper Found Trial 3 |
|---|---|---|---|
| 1 | 0.807 | 1.06 | 0.77 |
| 5 | 4.36 | 5.54 | 3.99 |
| 20 | 19.2 | 20.5 | 21.4 |
| 50 | 51.6 | 49.2 | 50.4 |
| 75 | 74.5 | 81.8 | 81.3 |
| 125 | 137 | 129 | 127 |
| 200 | 202 | 218 | 196 |

Based on the data presented in FIG. 9 and Table 3, copper concentration can be determined using AdSV with an accuracy and precision of 1.0 µg/L or ±10% (whichever is larger) in concentrations ranging from 1.0-200 µg/L.

Example 4

Sample Measurement

Figure 10:
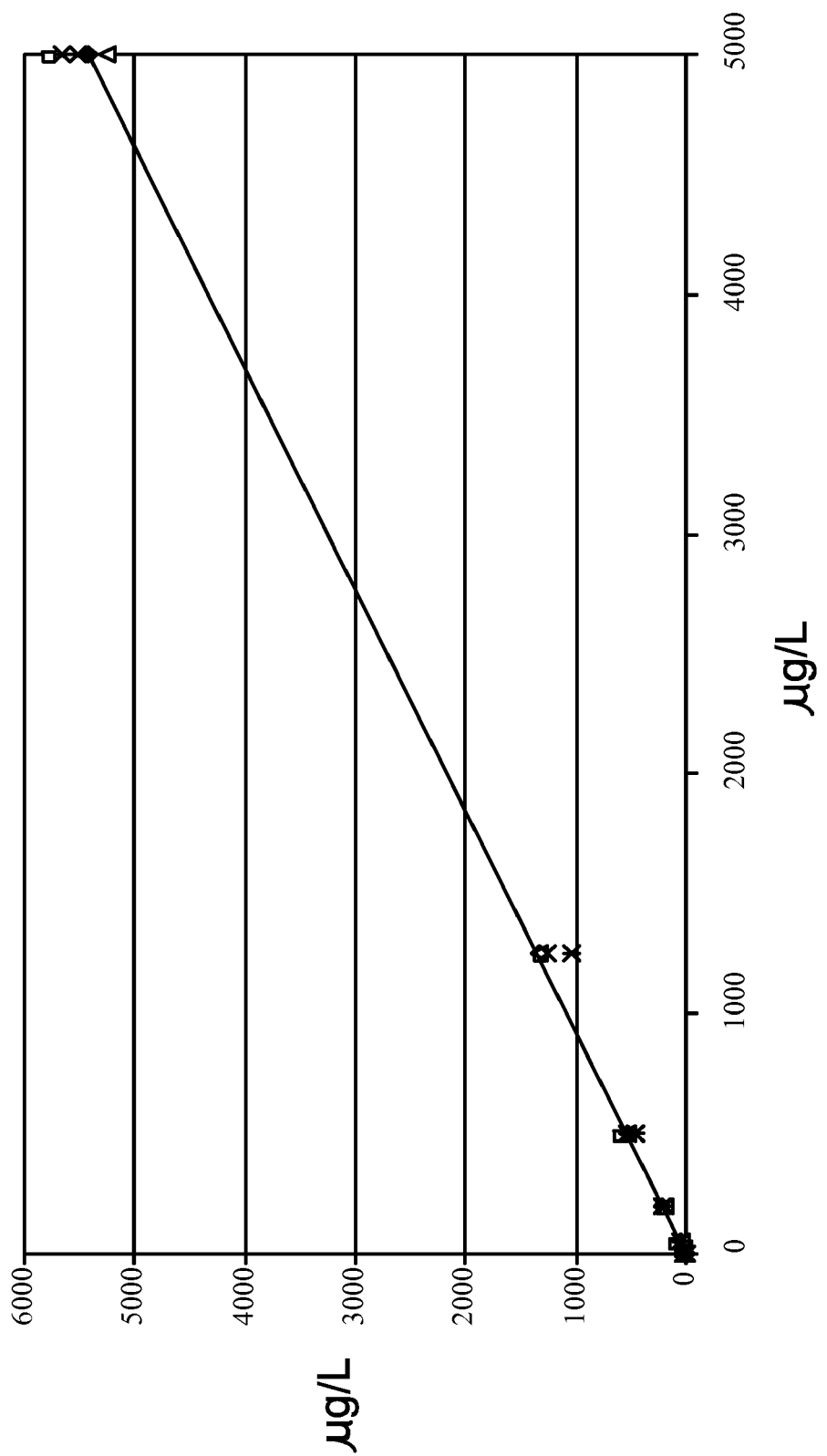
FIG. 10 is a graph showing the concentration of cobalt in spiked semiconductor process water determined by a representative device and method of the invention.

The system performance in real samples was demonstrated by the quantification of cobalt in semiconductor process water containing high amounts of interferences, such as organics, surfactants, and others using AdSV. The sample solution comprised 0.1 M buffer ammonia, DMG, and test spikes of 0, 20, 50, 200, 500, 1250, and 5000 µg/L cobalt. FIG. 10 is a voltammogram showing the cobalt concentration measured in five separate trials. In FIG. 10, the X-axis represents the amount of added cobalt (µg/L); the Y-axis represents the amount of cobalt detected (µg/L); y is equal to $1.0833x-3.2362$; and $R^2$ is equal to 0.9988. Table 4 shows the amount of cobalt added (µg/L) and the amount of cobalt found (µg/L) for each of the five trials corresponding to FIG. 10.

TABLE 4

| Cobalt Added | Co Found Trial 1 | Co Found Trial 2 | Co Found Trial 3 | Co Found Trial 4 | Co Found Trial 5 |
|---|---|---|---|---|---|
| 0 | 8.59 | 11.8 | 14.2 | 7.75 | 12.7 |
| 20 | 29 | 27.5 | 33.2 | 27.7 | 30.6 |
| 50 | 56.7 | 64.7 | 60.4 | 60 | 55.1 |
| 200 | 215 | 198 | 192 | 211 | 196 |
| 500 | 523 | 579 | 527 | 525 | 457 |
| 1250 | 1330 | 1300 | 1320 | 1270 | 1040 |
| 5000 | 5420 | 5750 | 5250 | 5650 | 5510 |

Based on the data presented in FIG. 10 and Table 4, it was found that a concentration of as low as 10 µg/L cobalt can be determined with an accuracy of 10 µg/L or ±15% (whichever is larger) in concentrations ranging from 10-5000 µg/L. Furthermore, continuous measurements in other samples (not shown) have demonstrated that the voltammetric system and method of the present invention have high overall stability and robustness in complex matrices.

While the one embodiment of the invention has been illustrated and described, it will be appreciated that various changes can be made therein without departing from the spirit and scope of the invention.

The embodiments of the invention in which an exclusive property or privilege is claimed are defined as follows:

1. An electroanalytic device, comprising:
   (a) an electroanalytical cell comprising a working electrode, an auxiliary electrode, a reference electrode, and a mercury chamber, wherein the reference electrode is disposed within a mercury-free portion of the mercury chamber;
   (b) a degassing system in fluid communication with the electroanalytical cell; and
   (c) a circulating means for continuously circulating a sample through the electroanalytical cell and the degassing system.

2. The device of claim 1, wherein the working electrode is a dropless mercury electrode.

3. The device of claim 1, wherein the auxiliary electrode is selected from the group consisting of mercury, glassy carbon, platinum, and gold.

4. The device of claim 1, wherein the reference electrode is selected from the group consisting of silver chloride and calomel.

5. The device of claim 1, wherein the degassing system comprises a degassing chamber.

6. The device of claim 1, wherein the degassing system comprises a heat source.

7. A system for voltammetric analysis, comprising:
   (a) a separation chamber for receiving a liquid sample solution;
   (b) an electroanalytical cell comprising a working electrode, an auxiliary electrode, a reference electrode, and a mercury chamber, wherein the reference electrode is disposed within a mercury-free portion of the mercury chamber;
   (c) a flow channel for providing fluid communication between the separation chamber and the electroanalytical cell;

(d) a degassing system for degassing the liquid sample solution, the degassing system in fluid communication with the electroanalytical cell and the separation chamber; and (e) a pump for circulating the liquid sample solution through the separation chamber, the electroanalytical cell, and the degassing system.

8. The system of claim 7, wherein the working electrode is a dropless mercury electrode disposed between the separation chamber and the mercury chamber.

9. The system of claim 7, wherein the auxiliary electrode comprises mercury contained in the mercury chamber.

10. The system of claim 7, wherein the separation chamber comprises a first sample inlet for receiving the liquid sample solution, a sample outlet for dispensing the liquid sample solution into the flow channel, a second sample inlet for receiving a degassed liquid sample solution from the degassing system, and a vent for releasing gas that has been separated from the degassed liquid sample solution.

11. The system of claim 7, wherein the flow channel is in fluid communication with a mercury channel for supplying mercury to the working electrode.

12. The system of claim 7, wherein the mercury chamber comprises a mercury chamber inlet for receiving the liquid sample solution and mercury from the flow channel, a first mercury chamber outlet for dispensing the liquid sample solution, and a second mercury chamber outlet for dispensing mercury to a mercury channel.

13. The system of claim 12, wherein the pump comprises a pump inlet in communication with the first mercury chamber outlet, and a pump outlet in communication with the degassing system.

14. The system of claim 13, wherein a rinse valve is disposed between the first mercury chamber outlet and the pump inlet.

15. The system of claim 13, wherein a drain valve is disposed between the pump outlet and the degassing system.

16. The system of claim 7, wherein the degassing system comprises a degassing chamber, an degassing inlet for receiving the liquid sample solution and a gas into the degassing chamber, and a degassing outlet for dispensing a degassed liquid sample solution and excess gas into the separation chamber.

17. A method for voltammetry, comprising the steps of:
(a) introducing a liquid sample solution into an electroanalytical cell of an electroanalytic device, wherein the electroanalytical device further comprises a degassing system and a pump;
(b) pumping the liquid sample solution through the electroanalytical cell to the degassing system;
(c) introducing an inert gas into the degassing system, thereby causing separation of dissolved gas from the liquid sample solution and providing a degassed liquid sample solution;
(d) pumping the degassed liquid sample solution into the electroanalytical cell; and
(e) making a voltammetric measurement of the degassed liquid sample solution.

18. The method of claim 17, wherein the electroanalytical cell comprises a working electrode, an auxiliary electrode, and a reference electrode.

19. The method of claim 18, wherein the inert gas is nitrogen gas.

20. The method of claim 17, wherein the degassing system comprises a degassing chamber.

21. The method of claim 20, wherein the degassing chamber is comprised of a chemically inert material.

22. The method of claim 17, wherein the degassing system further comprises a heat source.

23. The method of claim 17, wherein the degassing system further comprises a UV light source.

24. The method of claim 17, wherein the pump is operated in synchronization with the electroanalytical cell.

25. A method for voltammetric analysis of a liquid sample solution, comprising the steps of:
(a) introducing a liquid sample solution into a separation chamber of an electroanalytic device, wherein the electroanalytic device further comprises a degassing system and an electroanalytical cell;
(b) transferring the liquid sample solution into the degassing system;
(c) introducing an inert gas into the degassing system, wherein the inert gas contacts the liquid sample solution and provides a degassed liquid sample solution;
(d) transferring the degassed liquid sample solution from the degassing system into the separation chamber;
(e) transferring the degassed liquid sample solution from the separation chamber into a flow channel, wherein the flow channel provides fluid communication between the separation chamber and the electroanalytical cell, and wherein a working electrode is disposed within the flow channel; and
(f) making a voltammetric measurement of the degassed liquid sample solution.

26. The method of claim 25, wherein the liquid sample solution contains metal ions selected from the group consisting of Cu, Pb, Cd, Ni, Co, Fe, Se, Mo, Ti, Cr, and Sn.

27. The method of claim 25, wherein the working electrode is a dropless mercury electrode and further comprises a platinum wire for providing an electrical contact.

28. The method of claim 25, wherein the working electrode has a potential of between +0.3V to −2.2V relative to a reference electrode.

29. The method of claim 25, wherein the degassing system comprises a degassing chamber with an internal diameter of 0.2 to 2.0 millimeters.

30. The method of claim 25, wherein the inert gas is nitrogen gas.

31. The method of claim 25, wherein transferring the degassed liquid sample solution comprises pumping.

32. The method of claim 25, wherein mercury is transferred from a mercury chamber into the flow channel and forms a mercury meniscus at the working electrode.

33. The method of claim 25, wherein transfer of the degassed liquid sample solution into the flow channel and application of an accumulating potential to the working electrode causes metal ions contained in the degassed liquid sample solution to accumulate on the working electrode.

34. The method of claim 25, wherein making a voltammetric measurement of a degassed liquid sample solution is done by scanning the working electrode.

35. The method of claim 34, wherein after applying a measurement scan to the working electrode, the sample is transferred through the flow channel and into the mercury chamber.

36. The method of claim 34, wherein the sample propels mercury from the working electrode into the mercury chamber.

37. The method of claim 36, wherein the sample is transferred out of the mercury chamber and discarded through the drain valve.

* * * * *